(12) United States Patent
Horváth et al.

(10) Patent No.: US 8,437,002 B2
(45) Date of Patent: May 7, 2013

(54) IMAGING OPTICAL INSPECTION DEVICE WITH A PINHOLE CAMERA

(75) Inventors: Zoltán György Horváth, Budapest (HU); György Juhász, Budapest (HU); Miklós Fried, Budapest (HU); Csaba Major, Eger (HU); Péter Petrik, Budaörs (HU)

(73) Assignees: MTA TTK, Budapest (HU); MTA Wigner FK, Budapest (HU)

( * ) Notice: Subject to any disclaimer, the term of this patent is extended or adjusted under 35 U.S.C. 154(b) by 324 days.

(21) Appl. No.: 12/601,410

(22) PCT Filed: May 23, 2008

(86) PCT No.: PCT/HU2008/000058
§ 371 (c)(1),
(2), (4) Date: Jul. 15, 2010

(87) PCT Pub. No.: WO2008/142468
PCT Pub. Date: Nov. 27, 2008

(65) Prior Publication Data
US 2010/0296096 A1    Nov. 25, 2010

(30) Foreign Application Priority Data

May 23, 2007  (HU) .................................... 0700366

(51) Int. Cl.
*G01N 21/55* (2006.01)
*G01N 21/00* (2006.01)

(52) U.S. Cl.
USPC ................... 356/445; 356/237.1; 356/237.2

(58) Field of Classification Search ........... 356/445–448
See application file for complete search history.

(56) References Cited

U.S. PATENT DOCUMENTS

| 4,657,396 | A  | * | 4/1987  | Honda et al. ................. 356/394 |
| 4,770,530 | A  | * | 9/1988  | Van Aken et al. ............. 356/323 |
| 5,991,038 | A  | * | 11/1999 | Yamamoto .................... 356/600 |
| 7,145,654 | B2 | * | 12/2006 | Norton ......................... 356/369 |
| 7,349,091 | B2 | * | 3/2008  | Wada et al. ................... 356/369 |
| 2001/0021023 | A1 | * | 9/2001 | Ishikawa ...................... 356/445 |
| 2005/0073684 | A1 | * | 4/2005 | Norton .......................... 356/369 |

* cited by examiner

*Primary Examiner* — Michael P Stafira
(74) *Attorney, Agent, or Firm* — Jason D. Voight

(57) ABSTRACT

The invention relates to an imaging optical inspection setup for inspecting a sample (5). Said inspection setup comprises a source of light (3) illuminating a specified portion of the sample surface by non-collimated light (4) in a plane of illumination, at least one pinhole (7) arranged in a path of reflected light (4') reflected from said portion and/or in a path of transmitted light (4") travelling through the entire thickness of the sample (5) in said sample portion, said pinhole (7) extending at least in the plane of illumination, and at least one screen and/or at least one position-sensitive detector system (8) arranged in the path of light (4', 4") passing through said pinhole (7) and adapted to intercept said light (4', 4"), said detector system (8) being susceptible of sensing light intensity distribution along at least a line.

16 Claims, 3 Drawing Sheets

IMAGING OPTICAL INSPECTION DEVICE WITH A PINHOLE CAMERA

The invention relates to an imaging optical inspection device/setup, in particular to a reflectometric, polarimetric or ellipsometric setup with a hole/aperture (from now on "pinhole") camera. The imaging optical inspection setup according to the present invention is highly preferred when an extensive, non-destructive, as well as rapid and simple (qualifying) inspection of various materials, for example a (thin-)film(s) physically and/or chemically deposited onto a substrate is(are) to be performed. In particular, the imaging optical inspection setup according to the invention is suitable for the measuring of local optical properties of various samples and, on the basis of the obtained data, for a rapid and reliable mapping of physical properties of the samples inspected.

It is well-known that substances exposed to light alter the properties of the incident light to a great extent. Basically, vision is based on this feature; by means of processing the intensity of reflected light in an angle- or spectrum- (occasionally, mainly in the case of animals, polarization-) dependent manner, our brain gives information on the outside world—various components of the surroundings become identifiable in this way.

Reflectometry is a more "scientific" way of vision, it is one of the most well-spread species of optical inspection techniques. Reflectometry determines the change in intensity of the light reflected from the surface of the sample to be studied—in a number of cases, said light also interacts with the sample itself before exiting—as a function of the angles of incidence and reflection (and optionally also as a function of the spectrum of light), and then qualifies the sample itself on the basis of the obtained data. In certain cases, it can also be advantageous to study the relative polarization states of the incident and the reflected lights; this field is dealt with by polarimetry. A special field of polarimetry is ellipsometry wherein the angle dependence of polarization is considered. Moreover, in spectroellipsometers the wavelength dependence of polarization can be studied as well. All of these are such pieces of information that are characteristic to the composition and surface quality of the sample to be studied, and in some cases even to the bulk properties thereof near the surface.

Even by the most up-to-date apparatuses, reflection measurements, are performed in a localized manner, that is only in a single, tiny, well-defined portion (point) of the sample in every step, by exploiting a strictly parallel beam of light (having, in principle, zero divergence) and at a given angle of incidence (reflection) that can be arbitrarily chosen but remains the same. Then, the measurement can be repeated in a further point of the sample, e.g. by changing the sample position. If not only mean values over large areas are of importance, separate series of measurements carried out in a large number of various points are required for an analysis that also characterizes the extensive large areas locally. This is highly time consuming. Hence, conventional reflectometer constructions are totally inadequate for rapid sample analysis over large areas.

Nowadays, such position-sensitive linear detector rows and 2-dimensional detector arrays formed of a plurality of independent light sensors and producing real-time signals with a precision making said signals also suitable for measuring purposes are available that enable a position dependent and simultaneous measurement of much greater number of data than what was possible earlier. Known positions of the elements of the detector array can be used to measure either time (scanning), or angle (rotation), or spectrum (color dispersion), or even sample topography (imaging).

Problems linked up with the local measurement that can be carried out slowly by a single detector might be thus eliminated through the so-called imaging reflectometry (and/or polarimetry or ellipsometry), by means of which an image (that is, a set of position dependent reflection data) of even the whole sample surface might be obtained in a single step. A key element of such a solution is the line or array of detectors mentioned above, however, it is equally important to provide an adequate illumination system tailored to the given task.

When a photo or a video recording (that is, a time dependent series of photos) is taken, naturally, photos of a large sample (that is, a portion thereof falling within the camera angle) are captured, and hence, according to this approach, the "optical image forming apparatuses (reflectometers)" have already been existing for a long time. However, these apparatuses employ light path modifying devices, focussing systems, so-called lenses (and/or in certain cases non-planar mirrors) for the image forming. The essence of an image forming system based on refractive media of variable optical thickness and/or non-planar reflecting surfaces is that—in a simple and ideal case, putting it in the language of geometrical optics—every single point of the object plane is separately imaged to a respective point of the image plane. Brightness is enhanced by said image forming systems through collecting light rays emerging from a single object point at various angles and then concentrating them into one image point. As light emerging from the chosen object point at various angles adds up (integrates) in the respective image point, conventional optical image forming systems comprising light path modifying elements are, in principle, inadequate for the angle dependent analysis of reflected light since they average out the angle information.

In practice, this strict criterion does not always represent a drawback. When e.g. light of the Sun, which can be considered as a point source located in the infinity, reflected by the surface of the see is captured, an almost perfect image forming reflectometer is applied as the diameter of the lens limits the collection range of angles of the light incident to a respective point of the image plane from the points of the object (here the surface of the see) located almost in the infinity to a very small angle of view. That is, the critical angular range for the image forming detection is determined by the distance of the sample relative to the source of light and the aperture of the image forming system.

On the contrary, under laboratory and/or industrial conditions (where the reflection measurements are preferably take place) both the sample and the source of light are close to the detector, hence image forming reflectometry with angle integrating optical imaging cannot be used.

In very peculiar cases—from strictly planar surfaces of relatively large dimensions—it is possible to obtain images that can be evaluated, i.e. image forming reflectometry may work, however, in such cases a perfectly parallel beam of light with a large diameter should be used. Such a solution is described e.g. by U.S. Pat. No. 5,754,296 wherein an ellipsometer employing a collimated beam of light for measuring the thickness of a thin film sample is disclosed.

German Publication Pamphlet No. DE 197 45 945 A1 exemplifies reflectometric, in particular ellipsometric measurement of a sample by means of focussed light. Said measuring process embraces a relatively broad range of angles of incidence in a single step, however, the size of the surface examined decreases drastically—"image" can be obtained merely from a tiny sample area, the dimension of which falls into the order of the applied light's wavelength. Moreover, the chaotic behavior of polarization and beam distribution in the focal point of the optical elements highly encumbers the measurement and then the evaluation of data.

Hungarian Patent Appl. No. 0037290 discloses an actual imaging ellipsometer, wherein the sample is illuminated by a point-like source of light and the divergent light projection results in a non-focussed image on a screen or directly on a detector array along with keeping the angle dependence. A severe drawback of the apparatus is that only planar samples can be practically measured/qualified thereby. A further drawback of said apparatus is that the interfering background due to the internal light scattering induced by the individual elements cannot be filtered out, and hence, the measurement/qualifying of the sample must be performed in the presence of a relatively high noise.

It can be easily seen that imaging accomplished by means of a focussing system (such as, e.g. photography) would be apt for application in image forming reflectometers only in extreme cases since the precise angle dependence of reflection becomes unmeasurable in measuring systems of finite sizes, as appears in practice.

In view of the studies performed we came to a conclusion that the per se known pinhole (hole/aperture) camera ("camera obscura") offers an ideal means to accomplish an image forming reflectometer. (For the sake of simplicity, in what follows, the term "pinhole" accepted widely in international literature will be used instead of the term "circular apertured" that would be the correct term according to the terminology of optics.) The core of its functioning is that it allows the light reflected from the object to get to the screen, photographic plate or detector in a strictly angle dependent manner.

As a result of angle integration, solutions based on optical beam-shaping techniques (such as e.g. the imaging performed by optics with large apertures) increase the brightness of the imaging and due to their focussing property give "sharper" images of better resolution for some focal ranges. Their introduction to photography and e.g. to the field of astronomical observations was induced by the above described double advantage. Compared to image forming accomplished by a pinhole camera with a huge loss of light (which appears for high resolution and as a consequence of the very small size of the hole), images of greater detail and significantly greater brightness could be obtained by "lenses". It should, however, be noted that the term "imaging"—strictly speaking—can be used only in the case of light path modifying optical systems. The core feature of the functioning of the pinhole camera is that it allows only those rays of light that are unmodified in terms of their directions, i.e. that are so-called "straight" rays of light to reach a screen/detector. The pinhole camera thus realizes a linear projection of the object that also results in an image. Therefore, a process employing a pinhole camera could be even considered as an image forming process, but as it is obvious for a person skilled in the art, such a solution differs drastically in terms of its concept from conventional "imaging" in optics. The core of said difference is just the lack of angle integration, a requirement that is of high importance from the point of view of the present invention, a "price" of which is the poor brightness.

Despite of the significant amount of loss of light, the enhancement in detector sensitivity and the rapid increase in intensity of available sources of light made it actual and also reasonable to our days to employ systems with pinhole cameras for the purposes of photography and/or optical detection. The pinhole camera allows only a single "ray of light" (which is defined by the actual geometry and has got a very small angular domain) propagating at a given angle from every single object point to get the respective area of the detector system. Consequently, a given object point can be detected only at a single angle of incidence (reflection) at a time, however, different angles belong to each object point. The image captured as a single shot thus supplies angle dependent reflection data for a larger angular domain that corresponds to the camera angle of the system. By simply displacing the measuring system and the sample relative to one another, each object point might fall into the inspection domain specified, i.e. the entire angle dependent imaging can be achieved in a simple and rapid way.

It should be emphasized here, that in the case of a pinhole camera, no focus exists and there is no "definition" in the traditional sense. Hence, every component from which the incoming light gets through the pinhole appears in the image at a given angular resolution. If the source of illumination also falls into the detected angular range (as it is, in principle, unavoidable when e.g. planar samples are inspected), its "image" cannot be separated from the image of the sample which might cause a significant problem related to the measuring technique. Therefore, a customary pinhole camera, as such, is not an optical reflectometer. In view of the studies performed we came to a further conclusion that the applicability of optical reflectometers based on pinhole cameras also involves rather strict limitations regarding the special light sources (that in many cases should be tailored to the actual problem) used for illuminating the sample.

In light of the above, the present invention aims at providing an imaging optical inspection device/setup that is suitable for a rapid and reliable analysis of samples with large surfaces. In particular, the object of the present invention is to provide a reflectometer, polarimeter or ellipsometer that serves for the non-destructive measurement of local optical properties of extensive surfaces of various samples, as well as for the rapid and reliable mapping of physical properties of the inspected samples based on the obtained data.

The present invention is based on the recognition that the above objects can be achieved by measuring the polarization- and/or wavelength dependence of either the reflection taking place on the surface of the sample and/or the transmission through the material of the sample along with employing image forming realized by a pinhole camera and a simultaneous non-collimated (that is, diverging or converging) sample illumination. In this way, a relatively large surface can be inspected simultaneously at several angles of incidence in a single image.

The above objects to provide an imaging optical inspection setup are achieved by the inspection setup set forth in Claim 1. Possible further preferred embodiments of the inspection setup according to the invention are defined by Claims 2 to 13.

In particular, in the inspection setup according to the invention, the light reflected from or transmitted through a sample under study is led through a pinhole camera to the position-sensitive detector array (that can be a film, a camera, a row or array of photodetectors, etc.) arranged in the light path for further analysis. It is also possible to intercept said light on a screen and then, after an optical projection, to record the image appearing on the screen by an electronic or a traditional image recording means. The core of the invention is that the position- and angle-preserving projection/magnification of the sample surface (that can be considered as an image) is provided by a pinhole camera without the usage of further optical elements. As in the case of planar samples, due to the application of the pinhole camera, the angular range of measurement required in practice appears resolved in a planar geometrical position in a single section perpendicular to the surface under study, to achieve the above objects even a single row of detectors lying in said plane is adequate. As it is clear, in the case of planar samples to be typically inspected, when illumination is provided by a conventional collimated (parallel) beam and a pinhole camera is also used, reflection data on the whole sample could be obtained only from a single point, since such a setup would correspond to a classical reflectometer, ellipsometer. Thus, all advantage provided by the image forming would be lost. Consequently, in order that an image could be obtained from every single point of the sample, it is necessary to make use of a non-collimated illumination. Ideally, each object point should be illuminated from angles that correspond to all directions of the detected angular range to be studied (a homogeneous diffuse illumination of infinite size; a typical analogy of the closed, cloudy sky); however, at least within the angular range of capture of the pinhole camera, illumination of the object points should be provided by a specifically designed convergent source of light. As the detection angle of a photodetector is limited to an extent that depends on the detector size and the sample distance, said detection angle can be significantly increased by the simultaneous usage of several camera-detector systems and/or screens.

In the inspection setup according to the invention the pinhole is preferably arranged along the bisector of the cone angle of the angular range to be measured, as in this case the measurements can be performed over a symmetrical angular range.

In the inspection setup according to the invention the position-sensitive detector system (row or array of detectors) and/or the screen are preferably arranged in a plane essentially parallel to the sample to be measured, thereby obtaining a geometrically accurate image of the sample's measured portion.

In the inspection setup according to the invention the non-collimated illumination is preferably provided by a diffuse primary or secondary source of light (the latter in the form of e.g. an illuminated matted surface) having a size and located from the pinhole to a distance so as to fully cover at the place of the light source an area that is cut out by the detection cone angle range specified through the size of the detector system and/or screen and the distance of the pinhole relative to the detector system. In this way, the required homogeneous and diffuse illumination can be provided within the entire examination portion of the sample.

In the inspection setup according to the invention, to increase brightness, preferentially a convergent illumination corresponding to said detected cone angle is used, as a consequence of which the illumination, due to the insertion of suitable optical beam-shaping means, is "focussed" within the pinhole after being reflected by the sample. If the measurement is performed only at a single wavelength, even lenses of curved surface can be used. The usage of curved (on- or off-axis) parabolical or spherical mirrors that are insusceptible to dispersion, however, is much more preferred. When this latter type of optical beam-shaping means are used, the brightness of illumination can be optimally exploited at the imaging by a pinhole camera even in a multispectral case.

Furthermore, in the inspection setup according to the invention it is also preferred if a polarizer is inserted into at least one of the light paths extending from the light source to the sample and from the sample to the detector system. In this manner a sample dependent polarization state of optimal contrast can be ensured (for randomly or circularly polarized light sources). This state can be used for maximizing the sensitivity of inspection (for a simple reflection and/or transmission type of imaging) or it simply satisfies the minimum requirement for the performance of an ellipsometric measurement resulting in maximum amount of information. In most of the cases it is, of course, preferred to place movable polarizers into both the incident beam and the reflected and/or transmitted beam.

The inspection setup according to the invention is also suitable for performing measurements that should be carried out at multiple wavelengths. In such a case, preferably a temporal spectrum decomposition is applied, i.e. at a given instant only a light beam of a given wavelength (a single color component) is emitted from the geometrical place of the light source. When more than one monochromatic sources of light are present, this can be reached by e.g. changing said sources of light in the place of the illuminating light source in a time-controlled and alternating manner. When, in turn, a polychromatic (e.g. white-colored) source of light is used, this can be reached by inserting color filters of various transmission characteristics into the light path in front of either the light source or the detector system, one after the other, in a time-controlled and alternating manner. An acousto-optical deflector can be equally used.

The inspection setup according to the invention is also suitable for performing a measurement that should be carried out at multiple wavelengths at the same instant. In such a case, preferably a geometrical spectrum decomposition is performed by per se known dispersive means (prisms, gratings, acousto-optical decomposers, etc.) in such a way that, a slit is arranged in the path of the light beam emitted by the polychromatic source of light preferably in a plane parallel to the normal to the surface of the sample to be measured and the spectrum decomposition is performed in a plane perpendicular to this one. In this way a simultaneous angle and wavelength decomposition is realized. The optical means for decomposing the spectrum should be arranged in the light path extending between the pinhole and the detector system, and to assure detection at the individual wavelengths, said detector system must be provided in the form of a 2-dimensional detector system (eg. as a photodetector array).

In the inspection setup according to the invention, said sample under study is preferably arranged so as to be displaceable in a plane, at least along one line. In this way it can be assured that each point of the sample, at least along one line, at least once surely occupies a position in which it can be detected for each angle of the angular range detected. Thus, the relatively complicated scanning with respect to the detection angle can be transformed into a simple displacement.

Further advantages of the inventive solution, as well as further technical problems that can be solved by the application of the inventive solution will be apparent from the following description of the invention which is made in relation to the accompanied drawings, wherein the invention is described with reference to some of its preferred embodiments. Here, in the drawings FIG. 1 shows an embodiment of the imaging optical inspection setup according to the invention in a sectional view perpendicular to the surface of the sample to be inspected, said embodiment being suitable for the rapid inspection of the quality of the sample under study;

Figure 1:
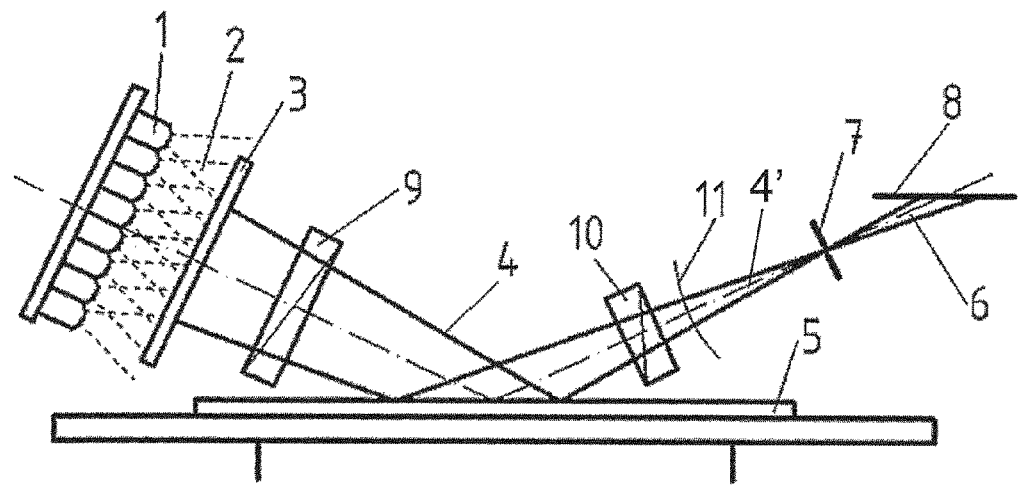

FIG. 1 illustrates a possible simple embodiment of the imaging optical inspection device according to the invention that is suitable for a rapid quality inspection of substances to be examined. Here, illuminating primary light source 1 according to the invention is provided by an extensive LED array of large surface that contains a plurality of individual LED elements and, optionally, is multicolored. Its primary light 2 propagates through a matted homogenizing light diffuser functioning as a virtual source of light 3. Sample 5 to be inspected is arranged in a suitably prepared sample holder (not shown). The surface of sample 5, which can be considered as a reflecting surface, is illuminated by non-collimated (i.e. non-parallel) light 4 generated by said diffuser. Non-collimated light 4' reflected by sample 5 travels through a pinhole 7 of desired size and, in this case, strikes the sensing surface of a position-sensitive detector system 8. Said position-sensitive detector system 8 is preferably provided by a CCD array, however, it can also be replaced by any other suitable means, for example by a photodetector that is suitable for the detection of light intensity distribution at least along a single line. The pinhole 7 is simply arranged in the path of the cone-like light 4' reflected by the inspected surface portion of the sample 5 in such a way that it falls just on the symmetry axis of the cone-like light beam, or rather in the sectional view, shown in FIG. 1, perpendicular to the sample's 5 surface on a bisector 6 of the light beams 4, 4'. In this arrangement of the pinhole 7, measurements can be performed over a symmetrical angular range. Said bisector 6 (shown by the dotted-dashed curve in FIG. 1) also defines a light path that extends from the virtual source of light 3, reflected by the inspected surface portion of said sample 5, through the pinhole 7 to the sensing surface of the detector system 8.

The polarization plane of light 4 striking sample 5 is preferably set by a polarizer 9 located on the illuminating side, while the polarization of reflected light 4' is determined by a polarizer 10, used as analyzer, located on the detector side, as is clear to a person skilled in the relevant art. Said polarizers 9, 10 are placed into various sections of said light path extending between the virtual source of light 3 and the sample 5, and between the sample 5 and the detector system 8, respectively. The polarizers 9, 10 are preferably film polarizers, although polarizers of different types can be equally used.

Sample 5 can be displaced in its own plane at least along a line, e.g. in such a way that the inspection setup of FIG. 1 is mounted onto a production line that moves continuously. Said displacement ensures that each point of the sample 5 passes through every possible angle value of a detection cone angular range 11 of non-collimated light 4 at least once, wherein said cone angular range 11 is determined by the dimensions of and the distance between the pinhole 7 and the position-sensitive detector system 8. To achieve geometrically accurate imaging, the position-sensitive detector system 8 is preferably arranged in a plane that is essentially parallel to the sample 5. Moreover, to process/evaluate the signals detected and/or to optionally store/display said signals, the position-sensitive detector system 8 is connected to a processing unit (not shown in the drawings), preferably to a computer.

Figure 2A:
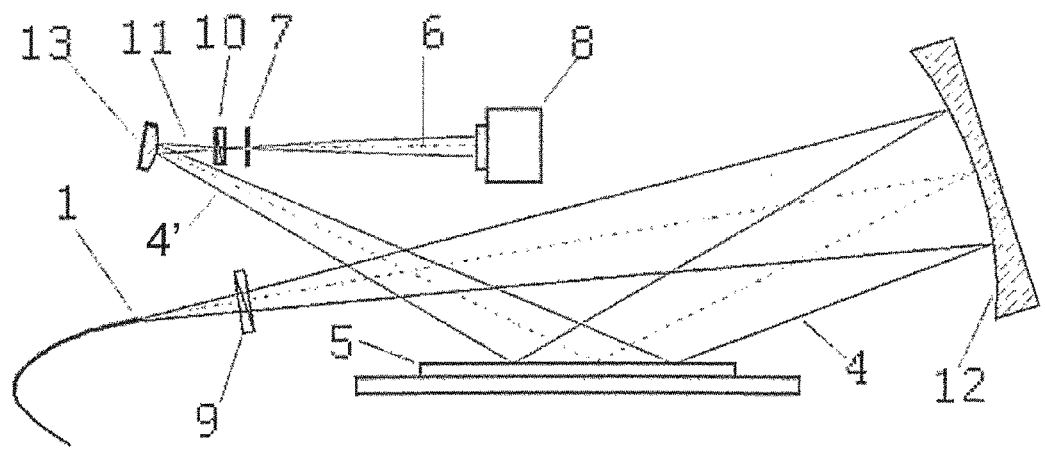
FIG. 2A illustrates another embodiment of the imaging optical inspection setup according to the invention in a sectional view perpendicular to the surface of the sample to be inspected, said embodiment being suitable for the rapid inspection of large sample surfaces by means of a light beam reflected by the sample.

FIG. 2A represents another embodiment of the imaging optical inspection setup according to the invention that accomplishes the simple and rapid quality inspection/measurement of substances to be examined over a large surface by means of a light beam reflected also by the sample surface. Here, the primary light source 1 according to the invention is provided by the exit aperture of an optical fiber. The primary light is shaped on a spherical mirror 12 functioning as the virtual source of light. The surface of sample 5, which can be considered as a reflecting surface, is illuminated by the non-collimated light 4 reflected by the spherical mirror 12. The (distortion) effect of the spherical mirror's 12 off-axis position on non-collimated light 4' reflected by the sample 5 is corrected/compensated by a cylindrical mirror 13 arranged on the bisector 6. After having been reflected by the cylindrical mirror 13, said non-collimated light 4' travels through the pinhole 7 arranged in its path and strikes the position-sensitive detector system 8. Said position-sensitive detector system 8 is preferably provided by e.g. a CCD array. In this case, the light path defined by said bisector 6 extends from the exit aperture of the optical fiber, reflected by the spherical mirror 12, the inspected surface portion of the sample 5 and the cylindrical mirror 13, through the pinhole 7 to the sensing surface of the position-sensitive detector system 8.

Similarly to the embodiment shown in FIG. 1, here the polarization plane of light 4 incident on sample 5 is preferably set by the polarizer 9 located on the illuminating side, while the polarization of light 4' reflected by sample 5 is determined by the polarizer 10, used as analyzer, located on the detector side, as is apparent to a person skilled in the relevant art. Said polarizers 9, 10 are preferably film polarizers, although polarizers of different types can be equally used.

Sample 5 is displaceable in its own plane at least along a line, e.g. in such a way that the inspection setup illustrated in FIG. 2A is mounted onto a production line that moves continuously. Said displacement ensures that each point of said sample 5 passes through every possible angle value of a detection cone angular range 11 of non-collimated light 4 at least once, wherein said cone angular range 11 is determined by the dimensions of and the distance between the pinhole 7 and the position-sensitive detector system 8. Furthermore, to process/evaluate the signals detected and/or to optionally store/display said signals, the position-sensitive detector system 8 is connected to a processing unit (not shown in the drawings), preferably to a computer.

Figure 2B:
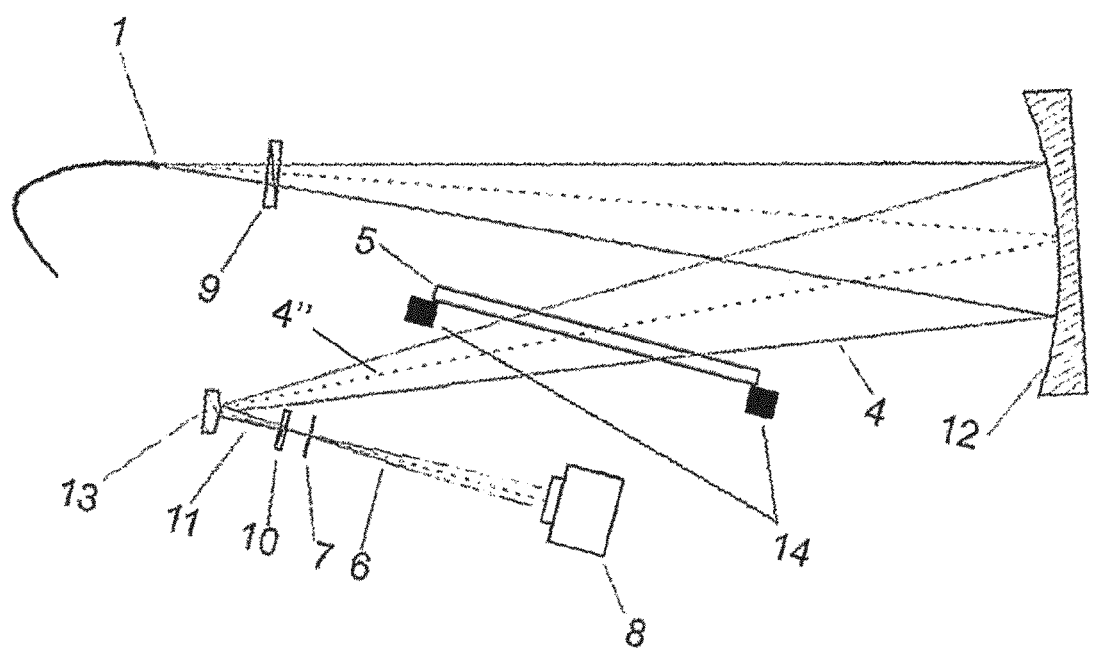
FIG. 2B shows a possible further embodiment of the imaging optical inspection setup according to the invention in a sectional view perpendicular to the surface of the sample to be inspected, said embodiment being suitable for the rapid inspection of large sample surfaces by means of a light beam transmitted by the sample.

FIG. 2B shows a yet further embodiment of the imaging optical inspection setup according to the invention that accomplishes the simple and rapid quality inspection/measurement of substances to be examined over a large surface by means of light 4" that has traveled through (i.e. transmitted by) the substance of the sample 5. The present embodiment differs from the inspection setup shown in FIG. 2A in that here it is light 4" transmitted by the sample 5 that travels through the pinhole 7 and strikes the position-sensitive detector system 8. For this, sample holder 14 supporting said sample 5 is preferably made of a material that is transparent at the wavelength of the light used for inspection and/or, as is shown in FIG. 2B, said sample holder 14 is preferably formed as a narrow supporting frame.

It should be noted, that light 4' reflected by sample 5 and light 4" transmitted by sample 5 can be used even simultaneously for the inspection of said sample if the embodiments of the inspection setup shown in FIGS. 2A and 2B are combined.

A major advantage of the structures shown in FIGS. 2A and 2B corresponding to the basic concept of point-like light source/polarizer/beam-shaping (focussing) optical means/ sample/beam-shaping (correcting) optical means/analyzer/pinhole/detector is that the diameters of the polarizers used do not limit the size of the sample surface to be measured simultaneously. Geometrical "expansion" of said structures can be simply realized by the application of a beam-shaping optical means having larger dimensions (i.e. a spherical mirror of larger radius).

A lower limit for the actual diameter of the pinhole 7 used in the inspection setup according to the invention is set by the diffraction limit (~100 μm). In turn, an upper limit for the diameter of the pinhole 7 is essentially determined by the size of the sample's 5 surface portion to be examined in a single step and the desired resolution at which the inspection is to be performed. It is also noted that for said inspection setup the interfering background can be almost fully eliminated through e.g. an appropriate arrangement of the pinhole 7 and the detector system 8 relative to each other and/or by accommodating the pinhole 7 and the detector system 8 within a common housing. In this latter case, the light admission opening of said common housing can be provided even by the pinhole 7 itself.

Figure 3A:
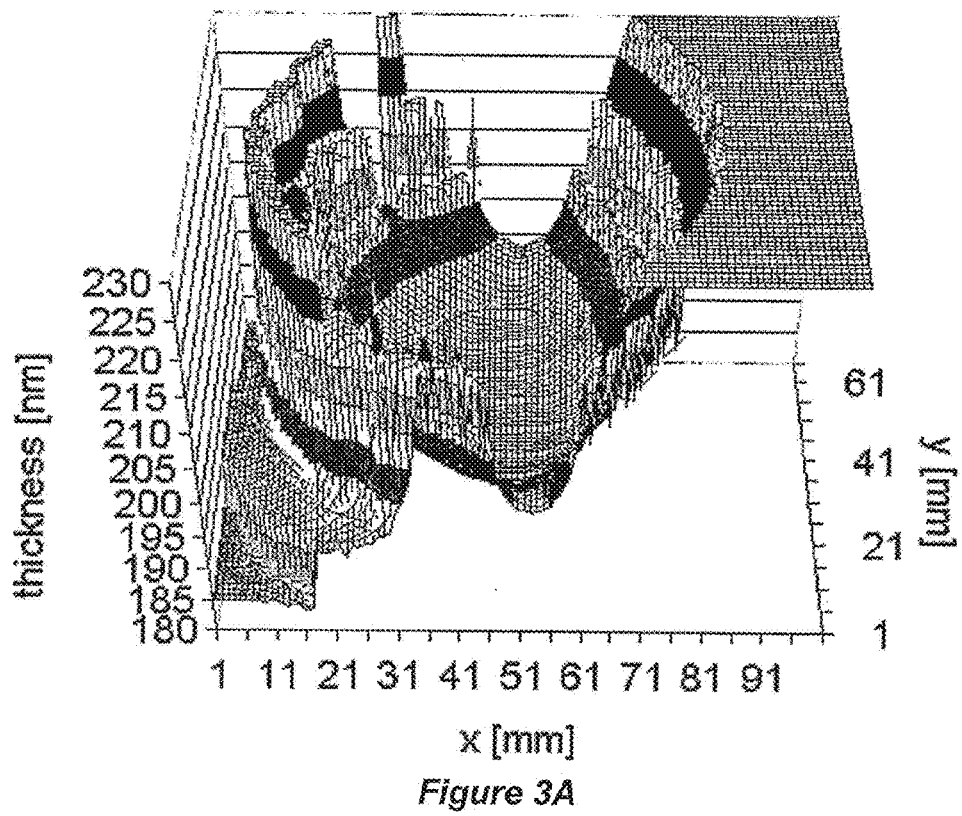
FIG. 3A is a thickness map of the poly-Si sublayer of a poly-Si/SiO$_2$ filmlayer structure applied onto a silicon (Si) wafer, taken by the inspection setup shown in FIG. 1.
Figure 3B:
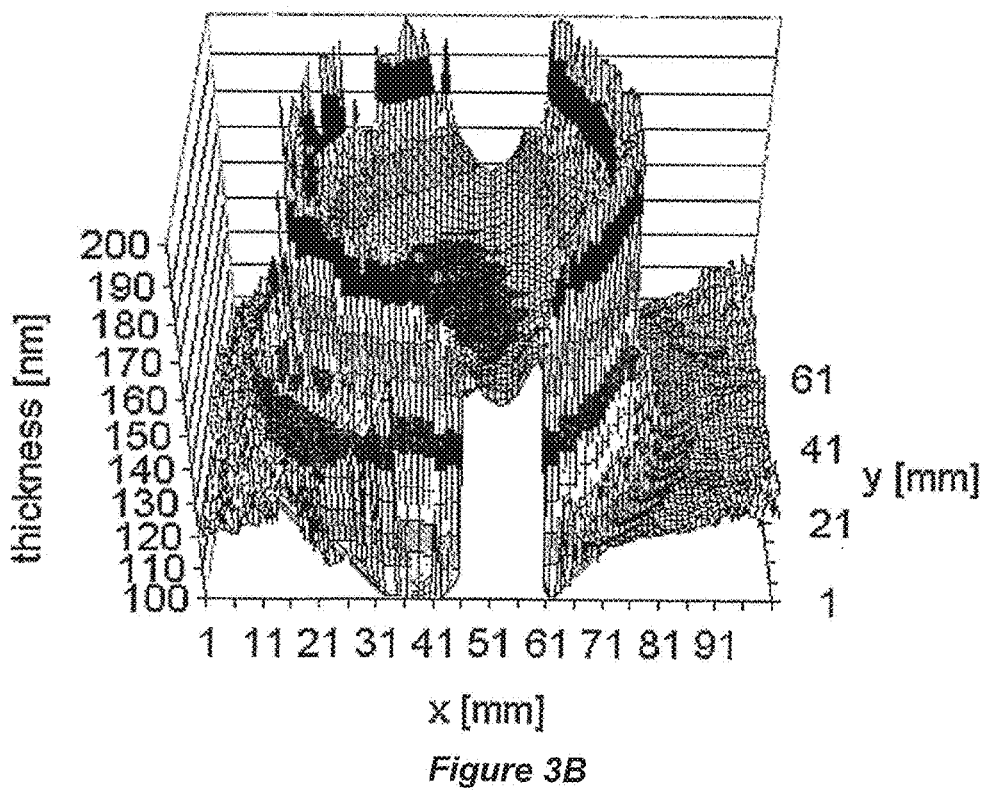
FIG. 3B is a thickness map of the SiO$_2$ sublayer of the poly-Si/SiO$_2$ filmlayer structure applied onto a silicon (Si) wafer, taken by the inspection setup shown in FIG. 1.

FIGS. 3A and 3B illustrate full ellipsometric thickness maps of the poly-Si sublayer (FIG. 3A) and the $SiO_2$ sublayer (FIG. 3B) of a poly-Si/$SiO_2$ filmlayer structure applied onto a silicon (Si) wafer of about 75 mm in diameter; said maps were taken by the inspection setup of FIG. 1. Here, a high intensity LED array (Luxeon Lumiled) emitting at three different wavelengths (637 nm, 523 nm, 460 nm) with small bandwidths (15 nm, 30 nm, 20 nm; respectively) was used as the light source 1, while the position-sensitive detector system 8 was provided by a computer-controlled monochrome digital camera of the Electrim 2000N type. The pixel number of the digital camera's CCD array is 652 by 494, each pixel has got the physical dimension of 7.5 μm by 7.5 μm. The angle limited lateral resolution over the surface of the sample 5 was 0.5 to 1 mm. As the resolution of the applied CCD array is much higher, the precision of the measurement could be enhanced through averaging over respective pixels of the CCD array. Furthermore, since several hundred points should be measured by a conventional ellipsometer to achieve the same lateral resolution, the inspection setup according to the present invention generally allows measurements that are performed about two orders of magnitude faster.

Positive effects of the imaging optical inspection setup (in particular, reflectometer, polarimeter or ellipsometer) according to the invention mostly appear in the graphical displayability of the measured data. The inspection setup with a pinhole camera operating with no distortion of the trace of the ray enables simultaneous measurements in a broad angular range, over a large surface of the sample under study. Pictorialness means simultaneous measurement of a plurality of sample points, and hence the inspection setup according to the invention decreases the measuring time by at least two orders of magnitude. Said decrease in measuring time enables, in turn, a real-time applicability (i.e. which is based not only on sampling) of the inspection setup on a production line (i.e. not in a laboratory), that have apparently significant economical advantages in actual practice.

It is also noted that the size of the image produced on the detector/screen can be easily controlled by altering the position of the pinhole within the light path extending between the light source and the sample: if the pinhole is approaching to the sample, the size of the image gradually increases, and vice versa.

The imaging optical inspection setup according to the invention can be preferably used to measure the quality and various physical/chemical parameters of a (thin-)film(s) deposited onto a substrate in a fast and precise manner, over relatively large sample surfaces. The setup at issue, thus, is highly preferred for the inspection of the thickness(es) and the optical refractive index(es) of the layer(s) deposited (and thereby the composition and/or structure thereof) and/or the changes of said parameters.

As is clear to a person skilled in the relevant art, various modifications can be effected in the imaging optical inspection setup according to the invention without exceeding the scope of protection set forth by the following set of claims.

The invention claimed is:

1. Imaging optical inspection setup for inspecting a sample (5), comprising a source of light (3) illuminating a specified portion of the sample surface by non-collimated light (4) in a plane of illumination, at least one pinhole (7) arranged in a path of reflected light (4') reflected from said portion of the sample (5), said pinhole (7) extending at least in the plane of illumination and transmitting said reflected light (4') in a position- and angle-preserving manner, and at least one screen and/or at least one position-sensitive detector system (8) arranged in the path of light (4') passing through said pinhole (7) and adapted to intercept said light (4'), said detector system (8) being susceptible of sensing light intensity distribution along at least a line.

2. The optical inspection setup according to claim 1, wherein the source of light (3) is provided in the form of a light diffuser illuminated by light of at least one wavelength emitted by a primary light source (1) that is provided in the form of a light emitter with a spatially extensive large surface.

3. The optical inspection setup according to claim 2, wherein the at least one screen and/or the at least one position-sensitive detector system (8) is/are arranged essentially parallel to the sample (5) to be inspected.

4. The optical inspection setup according to claim 1, wherein the source of light (3) is provided by a non-planar reflecting surface of a beam-shaping optical means (12) arranged in the path of light emitted by a point-like primary light source (1) at least at one wavelength and illuminated by said light.

5. The optical inspection setup according to claim 4, wherein at least one optical means (13) for compensating at least partially the distortion effects of the beam-shaping optical means (12) on the non-collimated light (4) is arranged in the path of light (4') reflected by the sample (5).

6. The optical inspection setup according to claim 1, wherein the spatial extension of the source of light (3) that provides the illumination by non-collimated light (4) is chosen so as to fully cover an area cut out at the place of said source of light (3) by a detection cone angular range (11) defined by the physical dimensions of the screen and/or the detector system (8) and the distance between the pinhole (7) and the detector system (8) in combination.

7. The optical inspection setup according to claim 1, wherein a polarizer (9; 10) is inserted into at least one of the light paths extending from the source of light (3) to the sample (5) and from the sample (5) to the position-sensitive detector system (8).

8. The optical inspection setup according to claim 1, wherein the primary light source (1) consists of monochromatic LEDs, wherein the LEDs emitting at a given wavelength emit simultaneously and then said emission takes place at every emission wavelength ore after the other in a controlled way.

9. The optical inspection setup according to claim 1, wherein the primary light source (1) is provided in the form of a polychromatic light source, and an acousto-optical deflector is arranged in or color filters of various given transmission characteristics are inserted into the light path extending between the source of light (3) that provides the illumination by non-collimated light (4) and the sample (5), wherein said insertion of the color fillers takes place in a controlled manner and alternating in time.

10. The optical inspection setup according to claim 9, wherein at least one elongated slit is inserted into the path of the light (4) emitted by the source of light (3) that provides the illumination by non-collimated light (4) before the sample (5) in a plane parallel to the normal to the surface of said sample (5), and a optical spectrum separator is arranged in the light path extending between the pinhole (7) and the detector system (8), and the position-sensitive detector system (8) is provided in the form of a 2-dimensional detector array.

11. The optical inspection setup according to claim 10, wherein the optical spectrum separator is formed by at least one of a prism, an optical grating and an acousto-optical deflector.

12. The optical inspection setup according to claim 1, wherein said sample (5) is arranged so as to be displaceable in its plane at least along a line.

13. The optical inspection setup according to claim 6, comprising a single pinhole (7) arranged on a bisector (6) of the detection cone angular range (11).

14. Imaging optical inspection method for inspecting a sample (5), comprising the steps of illuminating a specified portion of the sample surface by non-collimated light (4) in a plane of illumination;

arranging at least one pinhole (7) in a path of reflected light (4') reflected from said portion of the sample (5), said pinhole (7) extending at least in the plane of illumination and transmitting said reflected light (4') in a position- and angle-preserving manner;

arranging at least one screen and/or at least one position-sensitive detector system (8) in the path of light (4') passing through said pinhole (7), said detector system (8) being susceptible of sensing light intensity distribution along at least a line;

intercepting said reflected light (4'); and processing said reflected light (4') into signals for further manipulations.

15. The imaging optical inspection method according to claim 14, wherein said sample is provided in the form of a planar reflective surface.

16. The imaging optical inspection method according to claim 14, wherein quality and physical/chemical parameters, in particular the thickness and the optical refractive index, as well as the changes thereof, of at least one (thin)film deposited onto a substrate are derived from said signals.

* * * * *